US00PP22023P2

(12) United States Plant Patent
Dümmen

(10) Patent No.: US PP22,023 P2
(45) Date of Patent: Jul. 5, 2011

(54) ***SANVITALIA* PLANT NAMED 'DUESANSUGO'**

(50) Latin Name: *Sanvitalia procumbens*
Varietal Denomination: Duesansugo

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/653,960

(22) Filed: Dec. 21, 2009

(51) Int. Cl.
*A01H 5/00* (2006.01)

(52) U.S. Cl. ..... Plt./476

(58) Field of Classification Search ..... Plt./476
See application file for complete search history.

*Primary Examiner* — June Hwu
(74) *Attorney, Agent, or Firm* — C. A. Whealy

(57) ABSTRACT

A new and distinct cultivar of *Sanvitalia* plant named 'Duesansugo', characterized by its compact and mounding plant habit; vigorous growth habit; early and freely flowering habit; and inflorescences with bright yellow-colored ray florets.

1 Drawing Sheet

Botanical designation: *Sanvitalia procumbens.*
Cultivar denomination: 'DUESANSUGO'.

BACKGROUND OF THE INVENTION

The present invention relates to a new and distinct cultivar of *Sanvitalia* plant, botanically known as *Sanvitalia procumbens*, and hereinafter referred to by the name 'Duesansugo'.

The new *Sanvitalia* plant is a product of a planned breeding program conducted by the Inventor in Rheinberg, Germany. The objective of the breeding program is to create new compact and mounding *Sanvitalia* cultivars with numerous inflorescences.

The new *Sanvitalia* plant originated from an open-pollination in Rheinberg, Germany in July, 2007, of a proprietary selection of *Sanvitalia procumbens* identified as code number F-03-21, not patented, as the female, or seed, parent with an unknown selection of *Sanvitalia procumbens* as the male, or pollen, parent. The new *Sanvitalia* plant was discovered and selected by the Inventor as a single flowering plant from within the progeny of the stated open-pollination in a controlled greenhouse environment in Rheinberg, Germany in May, 2008.

Asexual reproduction of the new *Sanvitalia* plant by vegetative cuttings in a controlled environment in Rheinberg, Germany since May, 2008, has shown that the unique features of this new *Sanvitalia* plant are stable and reproduced true to type in successive generations.

SUMMARY OF THE INVENTION

Plants of the new *Sanvitalia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Duesansugo'. These characteristics in combination distinguish 'Duesansugo' as a new and distinct cultivar of *Sanvitalia:*

1. Compact and mounding plant habit.
2. Vigorous growth habit.

3. Early and freely flowering habit.
4. Inflorescences with bright yellow-colored ray florets.

Plants of the new *Sanvitalia* differ primarily from plants of the female parent selection in plant habit as plants of the new *Sanvitalia* are more compact than plants of the female parent selection.

Plants of the new *Sanvitalia* can be compared to plants of *Sanvitalia procumbens* 'Aztek Gold', not patented. In side-by-side comparisons conducted in Rheinberg, Germany, plants of the new *Sanvitalia* differed from plants of 'Aztek Gold' in the following characteristics:

1. Plants of the new *Sanvitalia* were more compact than plants of 'Aztek Gold'.
2. Plants of the new *Sanvitalia* had smaller leaves than plants of 'Aztek Gold'.
3. Plants of the new *Sanvitalia* had longer peduncles than plants of 'Aztek Gold'.

BRIEF DESCRIPTION OF THE PHOTOGRAPH

The accompanying photograph illustrates the overall appearance of the new *Sanvitalia* plant. The photograph shows the colors as true as it is reasonably possible to obtain in colored reproductions of this type. Colors in the photograph may differ slightly from the color values cited in the detailed botanical description which accurately describe the colors of the new *Sanvitalia* plant. The photograph comprises a side perspective view of a typical flowering plant of 'Duesansugo' grown in a container.

DETAILED BOTANICAL DESCRIPTION

The aforementioned photograph and following observations and measurements describe plants grown in 10.5-cm containers during the summer in a glass-covered greenhouse in Rheinberg, Germany under conditions and practices which approximate those generally used in commercial *Sanvitalia* production. During the production of the plants, day and night temperatures averaged 18° C. and light levels were about 4,500 lux. Plants were pinched one time three weeks after planting. Plants were 20 weeks old when the photograph and description were taken. In the following description, color references are made to The Royal Horticultural Society Colour Chart, 1995 Edition, except where general terms of ordinary dictionary significance are used.

Botanical classification: *Sanvitalia procumbens* 'Duesansugo'.

Parentage:

*Female parent.*—Proprietary selection of *Sanvitalia procumbens* identified as code number F-03-21, not patented.

*Male parent.*—Unknown selection of *Sanvitalia procumbens*, not patented

Propagation:

*Type.*—By vegetative cuttings.

*Time to initiate roots, summer.*—About five days at 20° C.

*Time to initiate roots, winter.*—About seven days at 20° C.

*Time to produce a rooted young plant, summer.*—About three weeks at 20° C.

*Time to produce a rooted young plant, winter.*—About four weeks at 20° C.

*Root description.*—Fine, fibrous; color, close to 155B.

*Rooting habit.*—Freely branching; moderately dense.

Plant description:

*Plant and growth habit.*—Compact, upright, outwardly spreading and mounding plant habit; vigorous growth habit.

*Branching habit.*—Freely branching habit with lateral branches potentially forming at every node.

*Plant height.*—About 9 cm.

*Plant diameter or spread.*—About 22 cm.

*Lateral branches.*—Length: About 12 cm. Diameter: About 2 mm. Strength: Strong. Texture: Pubescent. Color: Close to 144A.

Foliage description:

*Arrangement.*—Opposite, simple.

*Length.*—About 2.7 cm.

*Width.*—About 1.2 cm.

*Shape.*—Lanceolate to elliptical.

*Apex.*—Acute.

*Base.*—Obtuse.

*Margin.*—Entire.

*Texture, upper surface.*—Pubescent.

*Texture, lower surface.*—Smooth, glabrous.

*Venation pattern.*—Pinnate.

*Color.*—Developing leaves, upper surface: Close to 141A. Developing leaves, lower surface: Close to 144A to 144B. Fully expanded leaves, upper surface: Close to 137A; venation, close to 144C. Fully expanded leaves, lower surface: Close to 144A; venation, close to 144C.

*Petioles.*—Length: About 2.2 mm. Diameter: About 2.6 mm. Texture, upper and lower surfaces: Smooth, glabrous. Color, upper and lower surfaces: Close to 144C to 144D.

Inflorescence description:

*Appearance.*—Single (daisy) inflorescence form with ray and disc florets; inflorescences positioned above and beyond the foliar plane on strong peduncles; inflorescences face upright to outwardly.

*Flowering habit.*—Freely flowering habit; about 35 to 40 inflorescences per plant.

*Fragrance.*—Not detected.

*Natural flowering season.*—Plants flower continuously from April to October in Germany; early flowering habit, plants begin flowering about six weeks after planting.

*Inflorescence longevity.*—Inflorescences last about four days on the plant; inflorescences persistent.

*Inflorescence bud.*—Height: About 3 mm. Diameter: About 4 mm. Shape: Oblate. Color: Close to 144A.

*Inflorescence size.*—Diameter: About 1.6 cm. Depth (height): About 5 mm. Disc diameter: About 5 mm. Receptacle diameter: About 1 mm. Receptacle height: About 1 mm. Receptacle color: Close to 144B to 144C.

*Ray florets.*—Length: About 1.1 cm. Width: About 2.3 mm. Shape: Elliptical. Apex: Emarginate, obtuse. Base: Cordate, oblique. Margin: Entire. Texture, upper and lower surfaces: Smooth, glabrous; satiny. Number of ray florets per inflorescence: About twelve arranged in a single whorl. Color: When opening and fully opened, upper surface: Close to 9A; color does not fade with development. When opening and fully opened, lower surface: Close to 9B tinted with close to 144B.

*Disc florets.*—Shape: Tubular; apex dentate. Length: About 3 mm. Diameter: About 1 mm. Number of disc florets per inflorescence: About 50. Color, immature: Close to 144A. Color, mature: Apex: Close to 9A. Mid-section and base: Close to 144A.

*Phyllaries.*—Quantity per inflorescence: About ten to twelve in a single whorl. Length: About 4 mm. Width: About 3 mm. Shape: Ensiform. Apex: Acute. Base: Acute. Margin: Entire. Texture, upper and lower surfaces: Smooth, glabrous. Color, upper and lower surfaces: Close to 144A.

*Peduncles.*—Length: About 2.4 cm to 3.7 cm. Diameter: About 1 mm. Strength: Strong; flexible. Aspect: Upright to outwardly holding inflorescences beyond the foliar plane. Texture: Smooth, glabrous. Color: Close to 144A.

*Reproductive organs.*—Androecium (Present on disc florets only): Quantity per disc floret: Two. Filament length: About 0.5 mm. Filament color: Close to 144D. Anther shape: Oblong. Anther length: About 1 mm. Anther color: Close to 1A. Pollen amount: Scarce. Pollen color: Close to 2A. Gynoecium (Present on disc and ray florets): Quantity per ray floret and disc floret: One. Pistil length: About 2 mm. Style length: About 0.5 mm. Style color: Close to 1A. Stigma shape: Two-parted. Stigma color: Close to 1A. Ovary color: Close to 144B.

*Seeds.*—Quantity per inflorescence: About 50. Length: About 1 mm. Diameter: About 1 mm. Color: Close to 200B to 200C.

Disease/pest resistance: Plants of the new *Sanvitalia* have not been shown to be resistant to pathogens and pests common to *Sanvitalia*.

Garden performance: Plants of the new Clematis have exhibited good tolerance to rain and wind and have been observed to tolerate temperatures from about 5° C. to about 40° C.

It is claimed:

1. A new and distinct *Sanvitalia* plant named 'Duesansugo' as illustrated and described.

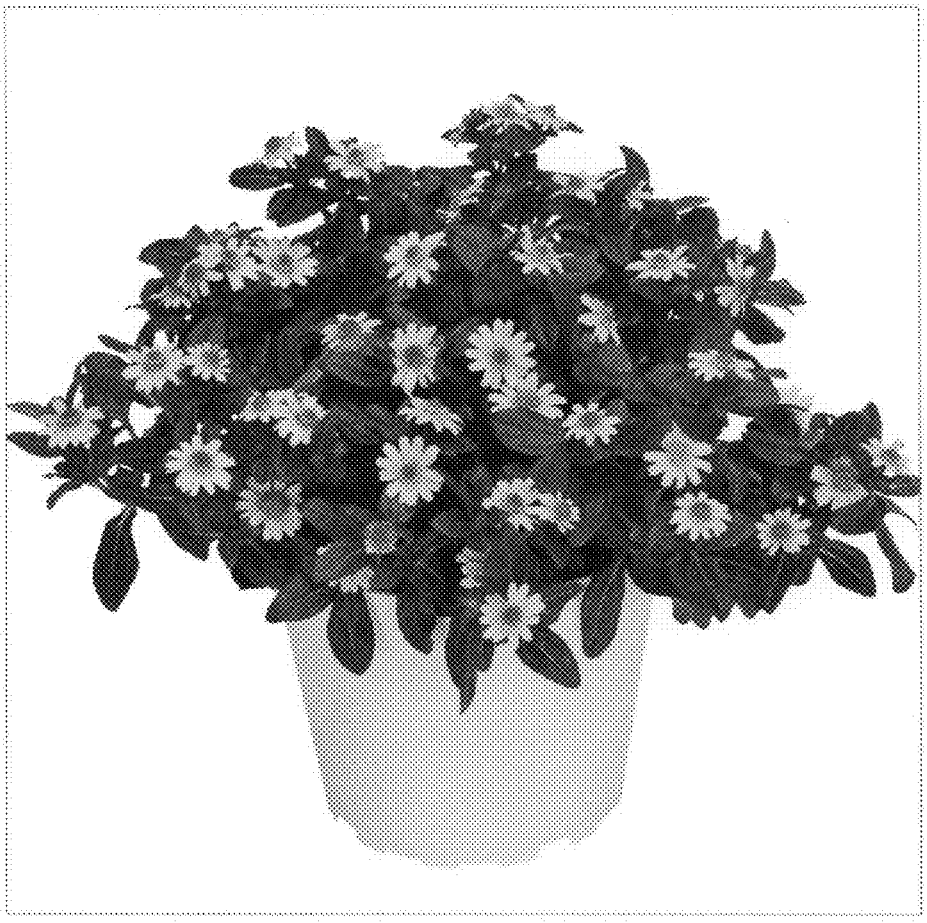

* * * * *